(12) United States Patent
Caponigro et al.

(10) Patent No.: US 10,328,066 B2
(45) Date of Patent: Jun. 25, 2019

(54) PHARMACEUTICAL COMBINATION COMPRISING THE PI3K INHIBITOR ALPELISIB AND THE CDK4/6 INHIBITOR RIBOCICLIB, AND THE USE THEREOF IN THE TREATMENT/PREVENTION OF CANCER

(71) Applicant: Novartis AG, Basel (CH)

(72) Inventors: Giordano Caponigro, Foxborough, MA (US); Thomas Horn-Spirohn, Cambridge, MA (US); Joseph Lehar, Lexington, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/755,140

(22) PCT Filed: Aug. 24, 2016

(86) PCT No.: PCT/IB2016/055043
§ 371 (c)(1),
(2) Date: Feb. 26, 2018

(87) PCT Pub. No.: WO2017/037575
PCT Pub. Date: Mar. 9, 2017

(65) Prior Publication Data
US 2018/0243280 A1 Aug. 30, 2018

Related U.S. Application Data

(60) Provisional application No. 62/211,018, filed on Aug. 28, 2015.

(51) Int. Cl.
*A61K 31/52* (2006.01)
*A61P 35/00* (2006.01)
*A61K 31/513* (2006.01)
*A61K 31/519* (2006.01)
*A61K 31/661* (2006.01)
*A61K 31/4439* (2006.01)
*A61K 31/5517* (2006.01)

(52) U.S. Cl.
CPC ........ *A61K 31/4439* (2013.01); *A61K 31/513* (2013.01); *A61K 31/519* (2013.01); *A61K 31/52* (2013.01); *A61K 31/5517* (2013.01); *A61K 31/661* (2013.01); *A61P 35/00* (2018.01)

(58) Field of Classification Search
CPC .............. A61K 31/4439; A61K 31/513; A61K 31/519; A61K 31/52; A61K 31/5517; A61K 31/661; A61K 35/00
See application file for complete search history.

(56) References Cited

U.S. PATENT DOCUMENTS

2014/0275067 A1* 9/2014 Sharpless ............. C07D 487/14
514/233.2

FOREIGN PATENT DOCUMENTS

WO 2013006532 1/2013
WO 2015022609 2/2015

OTHER PUBLICATIONS

Goodman & Gilman's 9th Edition (1996) 1225-1233.*
Vora Sadhna R et al. "CDK 4/6 Inhibitors sensitizePIK3CAMutant Breast Cancer to PI3K Inhibitors", Cancer Cell, vol. 26, No. 1, pp. 136-149, 2014.
Pishvaian, Michael J: "Abstract 5047:Synergistic anti-cancer activity of the CDK4/6 inhibitor PD-0332991 in combination with 5-fluorouracil-based chemotherapy in human colon cancer cells: Cancer Research", Cancer Research, 2010, Retrieved from the Internet: URL:http://Cancerres.aacrjournals.org/content/70/8_Supplement/5047 [retrieved on Oct. 24, 2016].

* cited by examiner

*Primary Examiner* — Shirley V Gembeh
(74) *Attorney, Agent, or Firm* — Sandra Rueck

(57) ABSTRACT

The present disclosure pertains to a pharmaceutical combination comprising (a) an alpha-isoform specific PI3K inhibitor, (b) a cyclin dependent kinase 4/6 (CDK4/6) inhibitor, and (c) an antimetabolite antineoplastic agent; combined preparations and pharmaceutical compositions thereof; the uses of such a combination in the treatment or prevention of cancer; and methods of treating or preventing cancer in a subject comprising administering a therapeutically effective amount of such combination.

2 Claims, 2 Drawing Sheets

PHARMACEUTICAL COMBINATION COMPRISING THE PI3K INHIBITOR ALPELISIB AND THE CDK4/6 INHIBITOR RIBOCICLIB, AND THE USE THEREOF IN THE TREATMENT/PREVENTION OF CANCER

FIELD OF THE INVENTION

The present disclosure relates to pharmaceutical combinations comprising (a) an alpha-isoform specific PI3K inhibitor (b) a cyclin dependent kinase 4/6 (CDK4/6) inhibitor, and (c) an antimetabolite antineoplastic agent; pharmaceutical compositions comprising the same; and methods of using such combinations and compositions in the treatment or prevention of cancer.

BACKGROUND OF THE INVENTION

Phosphatidylinositol 3-kinases (PI3Ks) comprise a family of lipid kinases that catalyze the transfer of phosphate to the D-3' position of inositol lipids to produce phosphoinositol-3-phosphate (PIP), phosphoinositol-3,4-diphosphate ($PIP_2$) and phosphoinositol-3,4,5-triphosphate ($PIP_3$) that, in turn, act as second messengers in signaling cascades by docking proteins containing pleckstrin-homology, FYVE, Phox and other phospholipid-binding domains into a variety of signaling complexes often at the plasma membrane (Vanhaesebroeck et al., *Annu. Rev. Biochem* 70:535 (2001); Katso et al., *Annu. Rev. Cell Dev. Biol.* 17:615 (2001)). Of the two Class 1 PI3Ks, Class 1A PI3Ks are heterodimers composed of a catalytic p110 subunit (α, β, δ isoforms) constitutively associated with a regulatory subunit that can be p85α, p55α, p50α, p85β or p55γ. The Class 1B sub-class has one family member, a heterodimer composed of a catalytic p110γ subunit associated with one of two regulatory subunits, p101 or p84 (Fruman et al., *Annu Rev. Biochem.* 67:481 (1998); Suire et al., *Curr. Biol.* 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B PI3K is activated directly by G protein-coupled receptors that bind a diverse repertoire of peptide and non-peptide ligands (Stephens et al., *Cell* 89:105 (1997)); Katso et al., *Annu. Rev. Cell Dev. Biol.* 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., *Cell* 64:281 (1991); Escobedo and Williams, *Nature* 335:85 (1988); Fantl et al., *Cell* 69:413 (1992)).

In many cases, PIP2 and PIP3 recruit Akt, the product of the human homologue of the viral oncogene v-Akt, to the plasma membrane where it acts as a nodal point for many intracellular signaling pathways important for growth and survival (Fantl et al., *Cell* 69:413-423 (1992); Bader et al., *Nature Rev. Cancer* 5:921 (2005); Vivanco and Sawyer, *Nature Rev. Cancer* 2:489 (2002)). Aberrant regulation of PI3K, which often increases survival through Akt activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110a isoform, PIK3CA, and for Akt are amplified and increased protein expression of their gene products has been demonstrated in several human cancers.

Furthermore, mutations and translocation of p85a that serve to up-regulate the p85-p110 complex have been described in human cancers. Finally, somatic missense mutations in PIK3CA that activate downstream signaling pathways have been described at significant frequencies in a wide diversity of human cancers (Kang at el., *Proc. Natl. Acad. Sci. USA* 102:802 (2005); Samuels et al., *Science* 304:554 (2004); Samuels et al., *Cancer Cell* 7:561-573 (2005)). These observations show that deregulation of phosphoinositol-3 kinase and the upstream and downstream components of this signaling pathway is one of the most common deregulations associated with human cancers and proliferative diseases (Parsons et al., *Nature* 436:792 (2005); Hennessey at el., *Nature Rev. Drug Disc.* 4:988-1004 (2005)).

It has been found that the 2-carboxamide cycloamino urea derivatives of the Formula (I) given below have advantageous pharmacological properties and inhibit, for example, PI3K (phosphatidylinositol 3-kinase). In particular, these compounds preferably show an improved selectivity for PI3K alpha with respect to beta and/or, delta and/or gamma subtypes. Hence, the compounds of Formula (I) are suitable, for example, to be used in the treatment of diseases depending on PI3 kinases (in particular PI3K alpha, such as those showing overexpression or amplification of PI3K alpha, or somatic mutation of PIK3CA), especially proliferative diseases such as tumor diseases and leukaemias.

Further, these compounds preferably show improved metabolic stability and hence reduced clearance, leading to improved pharmacokinetic profiles.

In addition, tumor development is closely associated with genetic alteration and deregulation of cyclin dependent kinases (CDKs) and their regulators, suggesting that inhibitors of CDKs may be useful anti-cancer therapeutics. Indeed, early results suggest that transformed and normal cells differ in their requirement for, e.g., cyclin D/CDK4/6 and that it may be possible to develop novel antineoplastic agents devoid of the general host toxicity observed with conventional cytotoxic and cytostatic drugs.

The function of CDKs is to phosphorylate and thus activate or deactivate certain proteins, including, e.g., retinoblastoma proteins, lamins, histone H1, and components of the mitotic spindle. The catalytic step mediated by CDKs involves a phospho-transfer reaction from ATP to the macromolecular enzyme substrate. Several groups of compounds (reviewed in, e.g., Fischer, P. M. Curr. Opin. Drug Discovery Dev. 2001, 4, 623-634) have been found to possess anti-proliferative properties by virtue of CDK-specific ATP antagonism.

At a molecular level, mediation of CDK/cyclin complex activity requires a series of stimulatory and inhibitory phosphorylation, or dephosphorylation, events. CDK phosphorylation is performed by a group of CDK activating kinases (CAKs) and/or kinases such as weel, Myt1 and Mik1. Dephosphorylation is performed by phosphatases such as Cdc25(a & c), PP2A, or KAP.

CDK/cyclin complex activity may be further regulated by two families of endogenous cellular proteinaceous inhibitors: the Kip/Cip family, or the INK family. The INK proteins specifically bind CDK4 and CDK6. $p16^{ink4}$ (also known as MTS1) is a potential tumor suppressor gene that is mutated or deleted in a large number of primary cancers. The Kip/Cip family contains proteins such as $p21^{Cip1,Waf1}$, p27$^{Kip1}$ and p57$^{kip2}$, where p21 is induced by p53 and is able to inactivate the CDK2/cyclin(E/A) complex. Atypically low levels of p27 expression have been observed in breast, colon and prostate cancers. Conversely, over-expression of cyclin E in solid tumors has been shown to correlate with poor patient prognosis. Over-expression of cyclin D1 has been associated with esophageal, breast, squamous, and non-small cell lung carcinomas.

The pivotal roles of CDKs, and their associated proteins, in coordinating and driving the cell cycle in proliferating cells have been outlined above. Some of the biochemical pathways in which CDKs play a key role have also been described.

In spite of numerous treatment options for cancer patients, there remains a need for effective and safe therapeutic agents and a need for their preferential use in combination therapy. In particular, there is a need for effective methods of treating or preventing cancers.

SUMMARY OF THE INVENTION

Provided herein is a pharmaceutical combination comprising (a) an alpha-isoform specific phosphatidylinositol 3-kinase (PI3K) inhibitor, (b) a CDK4/6 inhibitor, and (c) an antimetabolite antineoplastic agent.

In one aspect, provided herein is a pharmaceutical combination comprising:

(a) a compound having the structure of the formula (I)

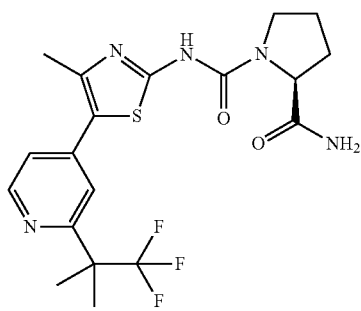

(I)

or a pharmaceutically acceptable salt thereof,
(b) a compound having the structure of Formula (II)

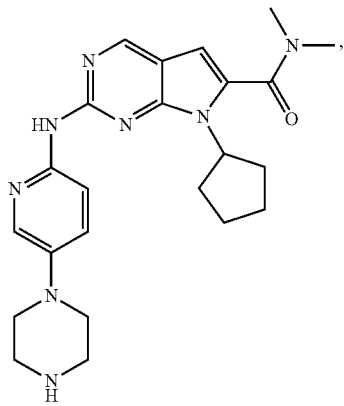

(II)

or a pharmaceutically acceptable salt thereof, and (c) an antimetabolite antineoplastic agent.

Combinations of the compound having the structure of Formula (I), or a pharmaceutically acceptable salt thereof, (b) a compound having the structure of Formula (II), or a pharmaceutically acceptable salt thereof, and (c) an antimetabolite antineoplastic agent, will also be referred to herein as a "combination of the invention."

In an embodiment of the pharmaceutical combination, the antimetabolite antineoplastic agent is selected from the group consisting of 5-fluorouracil, 5-fluorodeoxyuridine, 5-fluorodeoxyuridine monophosphate, cytarabine, 5-azacytidine, gemcitabine, mercaptopurine, azathioprine, thioguanine, pentostatin, erythrohydroxynonyladenine, fludarabine phosphate, cladribine, methotrexate, and pharmaceutically acceptable salts thereof.

In a further embodiment, the antimetabolite antineoplastic agent is 5-fluorouracil.

In an embodiment of the combination of the invention, the compound having the structure of Formula (I), the compound having the structure of Formula (II), and the antimetabolite antineoplastic agent are in the same formulation.

In another embodiment of the combination of the invention, the compound having the structure of Formula (I), the compound having the structure of Formula (II), and the antimetabolite antineoplastic agent are in two or more separate formulations.

In an embodiment, the combination is for simultaneous or sequential administration.

In another aspect, provided herein is a method for treating or preventing cancer in a subject in need thereof, comprising administering to the subject a therapeutically effective amount of the pharmaceutical combination of the invention.

In an embodiment, the cancer is a solid tumor.

In another embodiment, the cancer is selected from the group consisting of a benign or malignant tumor of the lung (including small cell lung cancer and non-small-cell lung cancer), bronchus, prostate, breast (including sporadic breast cancers and sufferers of Cowden disease), pancreas, gall bladder, gastrointestinal tract, colon, rectum, colon carcinoma, colorectal cancer, thyroid, liver, biliary tract, intrahepatic bile duct, hepatocellular, adrenal gland, stomach, gastric, central or peripheral nervous system (including astrocytoma, neuroblastoma, glioma, glioblastoma, and schwannoma), neuroendocrine, endometrial, kidney, renal pelvis, bladder, uterus, cervix, vagina, ovary, multiple myeloma, esophagus, nose, neck or head, brain, oral cavity and pharynx, larynx, small intestine, a melanoma, villous colon adenoma, a sarcoma (including osteosarcoma, fibrosarcoma or rhabdomyosarcoma, and Kaposi's sarcoma), a neoplasia, a neoplasia of epithelial character, a mammary carcinoma, basal cell carcinoma, squamous cell carcinoma, actinic keratosis, polycythemia vera, essential thrombocythemia, thyroid follicular cancer, a leukemia (including acute myelogenous leukemia, chronic myelogenous leukemia, lymphocytic leukemia, myeloid leukemia, meningeal leukemia, and promyelocytic leukemia), a lymphoma (including non-Hodgkin lymphoma, Hodgkin's lymphoma, mantle cell lymphoma, chronic lymphocytic leukaemia, B-cell lymphoma, T-cell lymphoma, hairy cell lymphoma, and Burkett's lymphoma), myelodysplastic syndrome, choriocarcinoma, rhabdoid cancer, seminoma, teratocarcinoma, xeroderma pigmentosum; retinoblastoma, keratoctanthoma, myelofibrosis with myeloid metaplasia, Waldenstroem disease, and Barret's adenocarcinoma.

In yet another embodiment, the cancer is colon cancer, rectal cancer, colorectal cancer, breast cancer, stomach cancer, or pancreatic cancer.

In another embodiment, the cancer is characterized by one or more of BRAF mutation, KRAS mutation, CDK4 mutation, CDK6 mutation, CDK4 overexpression, CDK6 overexpression, PIK3CA mutation, and PIK3CA overexpression.

In an embodiment, the pharmaceutical combination of the invention is for use in the treatment or prevention of cancer.

In an embodiment, the pharmaceutical combination of the invention for use in the preparation of a medicament for the treatment or prevention of cancer.

In an aspect, provided herein is the use of the pharmaceutical combination of the invention, for the manufacture of a medicament for the treatment or prevention of cancer.

In another aspect, provided herein is the use of the pharmaceutical combination of the invention for the treatment or prevention of cancer.

In an aspect, provided herein is a pharmaceutical composition comprising:

(a) a compound having the structure of the formula (I), or a pharmaceutically acceptable salt thereof, (b) a compound having the structure of Formula (II), or a pharmaceutically acceptable salt thereof, and (c) an antimetabolite antineoplastic agent.

In an embodiment of the pharmaceutical composition, the antimetabolite antineoplastic agent is selected from the group consisting of 5-fluorouracil, 5-fluorodeoxyuridine, 5-fluorodeoxyuridine monophosphate, cytarabine, 5-azacytidine, gemcitabine, mercaptopurine, azathioprine, thioguanine, pentostatin, erythrohydroxynonyladenine, fludarabine phosphate, cladribine, methotrexate, and pharmaceutically acceptable salts thereof.

In a further embodiment, the antimetabolite antineoplastic agent is 5-fluorouracil.

In another embodiment, the pharmaceutical composition provided herein further comprises one or more excipients.

DETAILED DESCRIPTION OF THE INVENTION

Figure 1:
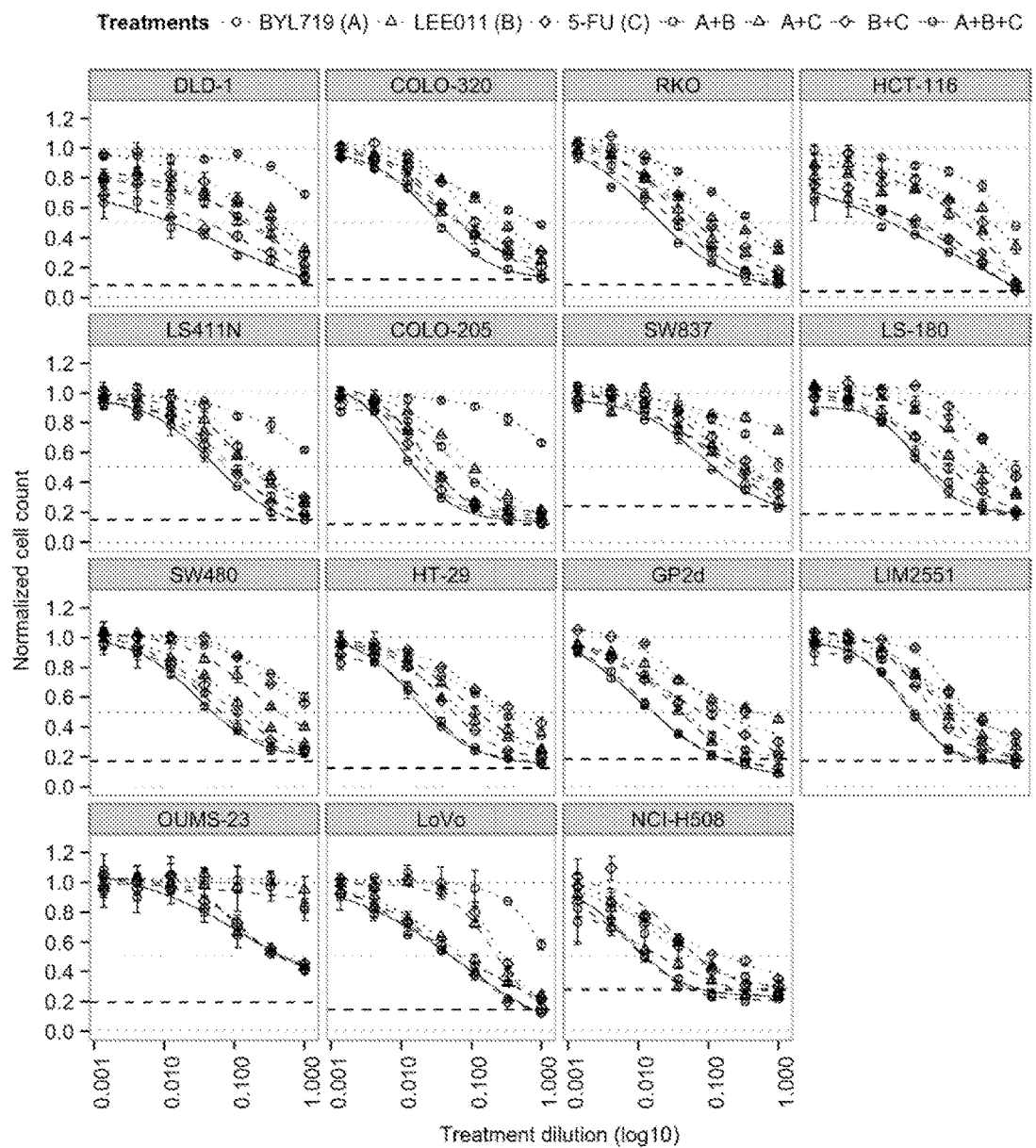
FIG. 1 shows dose-response curves for COMPOUND A (also referred to as BYL719), COMPOUND B (also referred to as LEE011), COMPOUND C (also referred to as 5-fluorouracil), A+B, A+C, B+C and A+B+C over 15 colorectal cancer cell lines. The x-axis indicates the log 10 of the treatment dilution; the y-axis indicates the cell count after treatment relative to DMSO. The strong dashed line indicates the number of cells before the start of the treatment ('baseline').

Provided herein is a pharmaceutical combination comprising (a) an alpha-isoform specific PI3K inhibitor (b) a cyclin dependent kinase 4/6 (CDK4/6) inhibitor, and (c) an antimetabolite antineoplastic agent. Specifically, provided herein is a pharmaceutical combination comprising:

(a) a compound having the structure of Formula (I)

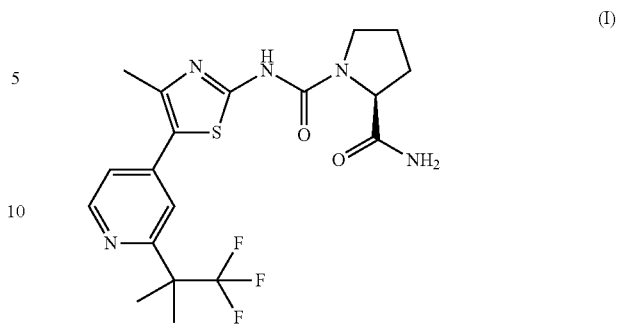

(I)

(also referred to herein as "Compound (I)", "COMPOUND A" or "BYL719")

or a pharmaceutically acceptable salt thereof, and (b) a compound having the structure of Formula (II)

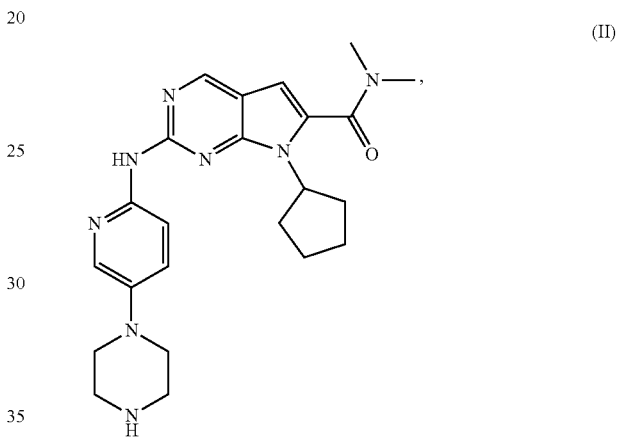

(II)

or a pharmaceutically acceptable salt thereof, and (c) an antimetabolite antineoplastic agent.

The pharmaceutical combination provided herein is, in particular, for use in the treatment or prevention of cancer. In one embodiment, the pharmaceutical combination provided herein is, in particular, for use in the treatment of cancer.

Certain terms used herein are described below. Compounds of the present invention are described using standard nomenclature. Unless defined otherwise, all technical and scientific terms used herein have the same meaning as is commonly understood by one of skill in the art to which this invention belongs.

The term "combination," "therapeutic combination," or "pharmaceutical combination" as used herein refer to either a fixed combination in one dosage unit form, or non-fixed combination, or a kit of parts for the combined administration where two or more therapeutic agents may be administered independently, at the same time or separately within time intervals, especially where these time intervals allow that the combination partners show a cooperative, e.g., synergistic, effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single formulation having a fixed ratio of active ingredients or in separate formulations (e.g., capsules and/or intravenous formulations) for each active ingredient. In addition, such administration also encompasses use of each type of therapeutic agent in a sequential or separate manner, either at approximately the same time or at different times. Regardless of whether the active ingredients are administered as a single formulation or in separate formulations, the drugs are administered to the same patient as part of the same course of therapy. In any case, the treatment regimen will provide beneficial effects in treating the conditions or disorders described herein.

The terms "alpha-isoform specific phosphatidylinositol 3-kinase inhibitor," "alpha-isoform specific PI3K inhibitor," "alpha-isoform selective phosphatidylinositol 3-kinase inhibitor," and "alpha-isoform selective PI3K inhibitor" as used herein refer to a compound that selectively targets, decreases, or inhibits at least one activity of the alpha-isoform of PI3K with respect to beta and/or delta and/or gamma subtypes. Exemplary alpha-isoform specific PI3K inhibitors are disclosed in International PCT Application WO2010/029082, which is hereby incorporated by reference in its entirety.

The terms "cyclin dependent kinase 4/6 inhibitor" and "CDK4/6 inhibitor" as used herein refer to a compound that selectively targets, decreases, or inhibits at least one activity of CDK4 and/or CDK6.

The term "antimetabolite antineoplastic agent" refers to phase specific anti-neoplastic agents that act at S phase (DNA synthesis) of the cell cycle by inhibiting DNA synthesis or by inhibiting purine or pyrimidine base synthesis and thereby limiting DNA synthesis.

The term "pharmaceutical composition" is defined herein to refer to a mixture or solution containing at least one therapeutic agent to be administered to a subject, e.g., a mammal or human, in order to prevent or treat a particular disease or condition affecting the mammal.

The term "pharmaceutically acceptable" as used herein refers to those compounds, materials, compositions and/or dosage forms, which are, within the scope of sound medical judgment, suitable for contact with the tissues of a warm-blooded animal, e.g., a mammal or human, without excessive toxicity, irritation, allergic response, and other problem complications commensurate with a reasonable benefit/risk ratio.

The terms "fixed combination," "fixed dose," and "single formulation" as used herein refers to a single carrier or vehicle or dosage form formulated to deliver an amount, which is jointly therapeutically effective for the treatment or prevention of cancer, of both therapeutic agents to a patient. The single vehicle is designed to deliver an amount of each of the agents, along with any pharmaceutically acceptable carriers or excipients. In some embodiments, the vehicle is a tablet, capsule, pill, or a patch. In other embodiments, the vehicle is a solution or a suspension.

The term "non-fixed combination," "kit of parts," and "separate formulations" means that at least one of the active ingredients (i.e., Compound (I), Compound (II), and the antimetabolite antineoplastic agent), are administered to a patient as a separate entity either simultaneously, concurrently, or sequentially with no specific time limits, wherein such administration provides therapeutically effective levels of the active ingredients in the body of the subject in need thereof.

The term "unit dose" is used herein to mean simultaneous administration of both agents together, in one dosage form, to the patient being treated. In some embodiments, the unit dose is a single formulation. In certain embodiments, the unit dose includes one or more vehicles such that each vehicle includes an effective amount of at least one of the agents along with pharmaceutically acceptable carriers and excipients. In some embodiments, the unit dose is one or more tablets, capsules, pills, injections, infusions, patches, or the like, administered to the patient at the same time.

An "oral dosage form" includes a unit dosage form prescribed or intended for oral administration.

The term "treating" or "treatment" as used herein comprises a treatment relieving, reducing, or alleviating at least one symptom in a subject or effecting a delay of progression of a disease. For example, treatment can be the diminishment of one or several symptoms of a disorder or complete eradication of a disorder, such as cancer. Within the meaning of the present disclosure, the term "treat" also denotes to arrest, delay the onset (i.e., the period prior to clinical manifestation of a disease), and/or reduce the risk of developing or worsening a disease. The term "protect" is used herein to mean prevent, delay, or treat, or all, as appropriate, development, continuance or aggravation of a disease in a subject, e.g., a mammal or human. The term "prevent", "preventing" or "prevention" as used herein comprises the prevention of at least one symptom associated with or caused by the state, disease or disorder being prevented.

The term "pharmaceutically effective amount," "therapeutically effective amount," or "clinically effective amount" of a combination of therapeutic agents is an amount sufficient to provide an observable or clinically significant improvement over the baseline clinically observable signs and symptoms of the disorders treated with the combination.

The term "jointly therapeutically active" or "joint therapeutic effect" as used herein means that the therapeutic agents can be given separately (in a chronologically staggered manner, especially a sequence-specific manner) in such time intervals that they prefer, in the warm-blooded animal, especially human, to be treated, still show an (preferably synergistic) interaction (joint therapeutic effect). Whether this is the case can, inter alia, be determined by following the blood levels of the compounds, showing that both compounds are present in the blood of the human to be treated at least during certain time intervals.

The term "subject" or "patient" as used herein is intended to include animals, which are capable of suffering from or afflicted with a cancer or any disorder involving, directly or indirectly, a cancer. Examples of subjects include mammals, e.g., humans, apes, monkeys, dogs, cows, horses, pigs, sheep, goats, cats, mice, rabbits, rats, and transgenic non-human animals. In an embodiment, the subject is a human, e.g., a human suffering from, at risk of suffering from, or potentially capable of suffering from cancers.

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The terms "about" or "approximately" are generally understood by persons knowledgeable in the relevant subject area, but in certain circumstances can mean within 20%, within 10%, or within 5% of a given value or range. Alternatively, especially in biological systems, the term "about" means within about a log (i.e., an order of magnitude) or within a factor of two of a given value.

As used herein, the PI3K inhibitor is (S)-Pyrrolidine-1, 2-dicarboxylic acid 2-amide 1-({4-methyl-5-[2-(2,2,2-trifluoro-1,1-dimethyl-ethyl)-pyridin-4-yl]-thiazol-2-yl}-amide) is a specific 2-carboxamide cycloamino urea derivative compound that potently and selectively targets the alpha (α)-isoform of class IA PI3K and has the following chemical structure:

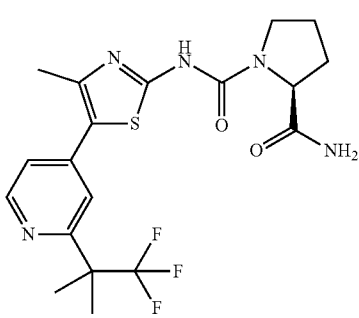

(I)

The compound having the structure of Formula (I) is also known in the art as alpelisib, and is referred to herein as "Compound (I)," "COMPOUND A," or "BYL719." For convenience, the group of the compound having the structure of Formula (I) and possible salts and solvates thereof is collectively referred to as Compound (I), meaning that reference to Compound (I) will refer to any of the compound or pharmaceutically acceptable salt or solvate thereof in the alternative.

Compound (I) and its pharmaceutically acceptable salts are described in PCT Application No. WO2010/029082, which is hereby incorporated by reference in its entirety, and methods of its preparation have been described, for example, in Example 15 therein. The preparation of Compound (I) is also described herein in Example 1. Preferably, Compound (I) is in the free base form. The salts of Compound (I) are preferably pharmaceutically acceptable salts; suitable counter-ions forming pharmaceutically acceptable salts are known in the field.

Compound (I) may be orally administered at an effective daily dose of about 1 to 6.5 mg/kg in human adults or children. Compound (I) may be orally administered to a 70 kg body weight human adult at a daily dosage of about 70 mg to 455 mg, e.g., about 200 to 400 mg, or about 240 mg to 400 mg, or about 300 mg to 400 mg, or about 350 mg to 400 mg, in a single dose or in divided doses up to four times a day. Preferably, Compound (I) is administered to a 70 kg body weight human adult at a daily dosage of about 350 mg to about 400 mg.

As used herein, the CDK 4/6 inhibitor 7-Cyclopentyl-2-(5-piperazin-1-yl-pyridin-2-ylamino)-7H-pyrrolo[2,3-d]pyrimidine-6-carboxylic acid dimethylamide (is referred to herein as the compound having the structure of formula (II):

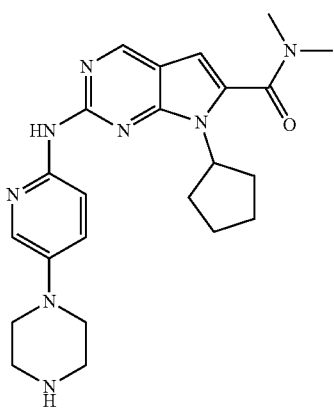

(II)

The compound having the structure of Formula (II) is also known in the art as ribociclib, and is referred to herein as "Compound (II)," "COMPOUND B," or "LEE011" For convenience, the group of the compound having the structure of Formula (II) and possible salts and solvates thereof is collectively referred to as Compound (II), meaning that reference to Compound (II) will refer to any of the compound having the structure of Formula (II) or a pharmaceutically acceptable salt or solvate thereof in the alternative. Compound (II) is described in PCT Application No. WO 2010/020675, which is hereby incorporated by reference in its entirety, as Example 74.

Compound (II) ("LEE011" or "ribociclib"), in general, is administered in a dose in the range from 10 mg to 2000 mg per day in human. in human. In one embodiment, LEE011 is administered 600 mg once daily. In another embodiment, LEE011 is administered 300 mg once daily. In another embodiment, LEE011 is administered in 900 mg once daily.

Antimetabolite antineoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite antineoplastic agents include, but are not limited to, 5-fluorouracil, methotrexate, cytarabine, mecaptopurine, thioguanine, and gemcitabine.

5-fluorouracil, also known as 5-fluoro-2,4-(1H,3H) pyrimidinedione, or 5-FU, is commercially available as fluorouracil. Administration of 5-fluorouracil leads to inhibition of thymidylate synthesis and is also incorporated into both RNA and DNA. The result typically is cell death. 5-fluorouracil may be administered intravenously, typically in a daily dose of between about 6 mg/kg and about 12 mg/kg, wherein the total amount is not in excess of 800 mg per day. 5-fluorouracil is indicated as a single agent or in combination with other chemotherapy agents in the treatment of carcinomas of the breast, colon, rectum, stomach and pancreas. Other fluoropyrimidine analogs include 5-fluorodeoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine).

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Other purine analogs include pentostatin, erythrohydroxynonyladenine, fludarabine phosphate, and cladribine.

Gemcitabine, 2'-deoxy-2', 2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer.

Methotrexate, N-[4[[(2,4-diamino-6-pteridinyl) methyl] methylamino] benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder.

Compound (I), Compound (II), and the antimetabolite antineoplastic agent, may be administered in the free form or in pharmaceutically acceptable salt form. A "pharmaceutically acceptable salt," as used herein, unless otherwise indicated, includes salts of acidic and basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmaceutically acceptable anions, such as the acetate, benzoate, bromide, chloride, citrate, fumarate, hydrobromide, hydrochloride, iodide, lactate, maleate, mandelate, nitrate, oxalate, salicylate, succinate, and tartrate salts. The preferred salt of Compound (II) is the succinate salt.

Unless otherwise specified, or clearly indicated by the text, reference to therapeutic agents useful in the pharmaceutical combination provided herein includes both the free base of the compounds, and all pharmaceutically acceptable salts of the compounds.

Provided herein is a combination therapy comprising an alpha-isoform selective PI3K inhibitor (Compound (I), or a pharmaceutically acceptable salt thereof), a CDK4/6 inhibitor (Compound (II), or a pharmaceutically acceptable salt thereof), and an antimetabolite antineoplastic agent (e.g., 5-fluorouracil). Administration of the combination includes administration of the combination in a single formulation or unit dosage form, administration of the individual agents of the combination concurrently but separately, or administration of the individual agents of the combination sequentially by any suitable route. The dosage of the individual agents of the combination can require more frequent administration of one of the agent(s) as compared to the other agent(s) in the combination. Therefore, to permit appropriate dosing, packaged pharmaceutical products can contain one or more dosage forms that contain the combination of agents, and one or more dosage forms that contain one of the combination of agents, but not the other agent(s) of the combination.

The present invention particularly pertains to a combination of the invention for treating or preventing cancer. In an embodiment, the combination of the invention is used for the treatment or prevention of cancer comprising administering to the subject a combination therapy, comprising an effective amount of a compound having the structure of Formula (I), or a pharmaceutically acceptable salt thereof, an effective amount of a compound having the structure of Formula (II), and an effective amount of antimetabolite antineoplastic agent (e.g., 5-fluorouracil). Preferably, these compounds are administered at therapeutically effective dosages which, when combined, provide a beneficial effect. The administration may be separate, simultaneous, or sequential. In an embodiment, the administration is simultaneous or sequential.

Thus, in an embodiment, the combination of the invention is for use in the treatment or prevention of cancer. In an embodiment, the combination is for use in the treatment of cancer.

Also provided herein is a use of the combination of the invention for the treatment or prevention of cancer. In an embodiment, the use of the combination is for the treatment of cancer.

In an embodiment, the cancer is a solid tumor. The term "solid tumor" especially means melanoma, breast cancer, ovarian cancer, colorectal cancer, and generally gastrointestinal tract, cervix cancer, lung cancer (including small-cell lung cancer and non-small cell lung cancer), head and neck cancer, bladder cancer, or prostate cancer. The present combination inhibits the growth of solid tumors and also liquid tumors. Further, depending on the tumor type and particular combination used, a decrease of the tumor volume can be obtained. The combination of the invention disclosed herein is also suited to prevent the metastatic spread of tumors and the growth or development of micrometastases. The combination of the invention disclosed herein is suitable for the treatment of poor prognosis patients, especially such poor prognosis patients having colon cancer, rectal cancer, colorectal cancer, breast cancer, stomach cancer or pancreatic cancer.

In another embodiment of any of the pharmaceutical combinations provided herein, the cancer is selected from a benign or malignant tumor of the lung (including small cell lung cancer and non-small-cell lung cancer), bronchus, prostate, breast (including sporadic breast cancers and sufferers of Cowden disease), pancreas, gall bladder, gastrointestinal tract, colon, rectum, colon carcinoma, colorectal cancer, thyroid, liver, biliary tract, intrahepatic bile duct, hepatocellular, adrenal gland, stomach, gastric, central or peripheral nervous system (including astrocytoma, neuroblastoma, glioma, glioblastoma, and schwannoma), neuroendocrine, endometrial, kidney, renal pelvis, bladder, uterus, cervix, vagina, ovary, multiple myeloma, esophagus, nose, neck or head, brain, oral cavity and pharynx, larynx, small intestine, a melanoma, villous colon adenoma, a sarcoma (including osteosarcoma, fibrosarcoma or rhabdomyosarcoma, and Kaposi's sarcoma), a neoplasia, a neoplasia of epithelial character, a mammary carcinoma, basal cell carcinoma, squamous cell carcinoma, actinic keratosis, polycythemia vera, essential thrombocythemia, thyroid follicular cancer, a leukemia (including acute myelogenous leukemia, chronic myelogenous leukemia, lymphocytic leukemia, myeloid leukemia, meningeal leukemia, and promyelocytic leukemia), a lymphoma (including non-Hodgkin lymphoma, Hodgkin's lymphoma, mantle cell lymphoma, chronic lymphocytic leukaemia, B-cell lymphoma, T-cell lymphoma, hairy cell lymphoma, and Burkett's lymphoma), myelodysplastic syndrome, choriocarcinoma, rhabdoid cancer, seminoma, teratocarcinoma, xeroderma pigmentosum; retinoblastoma, keratoctanthoma, myelofibrosis with myeloid metaplasia, Waldenstroem disease, and Barret's adenocarcinoma.

In another embodiment, the cancer is colon cancer, rectal cancer, colorectal cancer, breast cancer, stomach cancer, or pancreatic cancer.

In another embodiment, the cancer is characterized by one or more of BRAF mutation, KRAS mutation, CDK4 mutation, CDK6 mutation, CDK4 overexpression, CDK6 overexpression, PIK3CA mutation, and PIK3CA overexpression. In a further embodiment, the cancer is characterized by activating mutations in one or more of BRAF, KRAS, CDK6, CDK4, and PIK3CA.

The nature of cancer is multifactorial. Under certain circumstances, drugs with different mechanisms of action may be combined. However, just considering any combination of therapeutic agents having different mode of action does not necessarily lead to combinations with advantageous effects.

The administration of a pharmaceutical combination of the invention may result not only in a beneficial effect, e.g. a synergistic therapeutic effect, e.g. with regard to alleviating, delaying progression of or inhibiting the symptoms, but also in further surprising beneficial effects, e.g. fewer side-effects, more durable response, an improved quality of life or a decreased morbidity, compared with a monotherapy applying only one of the pharmaceutically therapeutic agents used in the combination of the invention.

A further benefit is that lower doses of the therapeutic agents of the combination of the invention can be used, for example, such that the dosages may not only often be smaller, but also may be applied less frequently, or can be used in order to diminish the incidence of side-effects observed with one of the combination partners alone. This is in accordance with the desires and requirements of the patients to be treated.

It can be shown by established test models that a combination of the invention results in the beneficial effects described herein before. The person skilled in the art is fully enabled to select a relevant test model to prove such beneficial effects. The pharmacological activity of a combination of the invention may, for example, be demonstrated in a clinical study or in an animal model.

In determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients may render impractical the use of this form of testing as a primary model for synergy. However, the observation of synergy in certain experiments (see, e.g., Example 2) can be predictive of the effect in species, and animal models that exist may be used to further quantify a synergistic effect. The results of such studies can also be used to predict effective dose ratio ranges and the absolute doses and plasma concentrations.

In an embodiment, the combination or composition, or both, provided herein display a synergistic effect. The term "synergistic effect" as used herein, refers to action of two [or more] agents such as, for example, Compound (I), or a pharmaceutically acceptable salt thereof, Compound (II), or a pharmaceutically acceptable salt thereof, and an antimetabolite antineoplastic agent, to produce an effect, for example, slowing the symptomatic progression of cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively. An additional method to show the synergistic effect is the highest single agent model (HSA) as null hypothesis (Berenbaum 1989). Excess over the HSA model predicts a functional connection between the inhibited targets (Lehar, Zimmermann et al. 2007, Lehar, Krueger et al. 2009). This method results in an indicator for the strength of the combination, $z_c$ (see, e.g., Example 2, including Table 2 for the $z_c$ scores of certain embodiments of the combination of the invention).

In a further embodiment, the present invention provides a synergistic combination for administration to humans comprising the combination of the invention, where the dose range of each component corresponds to the synergistic ranges suggested in a suitable tumor model or clinical study.

In another aspect, provided herein is a pharmaceutical composition such as a combined preparation or a pharmaceutical composition which comprises (a) Compound (I), or a pharmaceutically acceptable salt thereof, (b) Compound (II), or a pharmaceutically acceptable salt thereof, and (c) an antimetabolite antineoplastic agent.

In an embodiment, the antimetabolite antineoplastic agent is selected from the group consisting of 5-fluorouracil, 5-fluorodeoxyuridine, 5-fluorodeoxyuridine monophosphate, cytarabine, 5-azacytidine, gemcitabine, mercaptopurine, azathioprine, thioguanine, pentostatin, erythrohydroxynonyladenine, fludarabine phosphate, cladribine, methotrexate, and pharmaceutically acceptable salts thereof.

In a further embodiment, the antimetabolite antineoplastic agent is 5-fluorouracil.

In an embodiment of any of the pharmaceutical compositions provided herein, the composition further comprises one or more excipients. In a further embodiment, the pharmaceutical composition further comprises one or more pharmaceutically acceptable excipients.

As used herein, the term "pharmaceutically acceptable excipient" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The pharmaceutical compositions for the administration in a fixed combination, i.e., a single galenical composition comprising the combination of the invention, may be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g., as indicated above, or in combination with one or more pharmaceutically acceptable carriers, especially suitable for enteral or parenteral application.

The pharmaceutical composition may contain, from about 0.1% to about 99.9%, preferably from about 1% to about 60%, of the therapeutic agent(s). Suitable pharmaceutical compositions for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of various conventional mixing, comminution, direct compression, granulating, sugar-coating, dissolving, lyophilizing processes, melt granulation, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units.

In an aspect, provide herein is a use of the combination of the invention for the manufacture of a medicament for the treatment or prevention of cancer. In an embodiment, the use of the pharmaceutical combination is for the manufacture of a medicament for the treatment of cancer.

Also provided herein is the combination of the invention for use in the preparation of a medicament for the treatment or prevention of cancer. In an embodiment, the combination is for use in the preparation of a medicament for the treatment of cancer.

A therapeutically effective amount of each of the combination partner of the combination of the invention may be administered simultaneously or sequentially and in any order, and the components may be administered as the same formulation, or as separate formulations.

The effective dosage of each of the combination partners employed in the combination of the invention may vary depending on the particular compound or pharmaceutical composition employed, the mode of administration, the condition being treated, and the severity of the condition being treated. Thus, the dosage regimen of the combination of the invention is selected in accordance with a variety of factors including the route of administration and the renal and hepatic function of the patient.

The optimum ratios, individual and combined dosages, and concentrations of the combination partners (Compound (I), or a pharmaceutically acceptable salt thereof, Compound (II), or a pharmaceutically acceptable salt thereof, and an antimetabolite antineoplastic agent (e.g., 5-fluorouracil)) of the combination of the invention that yield efficacy without toxicity are based on the kinetics of the therapeutic agents' availability to target sites, and are determined using methods known to those of skill in the art.

The effective dosage of each of the combination partners may require more frequent administration of one of the compound(s) as compared to the other compound(s) in the combination. Therefore, to permit appropriate dosing, packaged pharmaceutical products may contain one or more dosage forms that contain the combination of compounds, and one or more dosage forms that contain one of the combination of compounds, but not the other compound(s) of the combination.

When the combination partners, which are employed in the combination of the invention, are applied in the form as marketed single drugs, their dosage and mode of administration can be in accordance with the information provided on the package insert of the respective marketed drug, if not mentioned herein otherwise.

The optimal dosage of each combination partner for treatment or prevention of a cancer can be determined empirically for each individual using known methods and will depend upon a variety of factors, including, though not limited to: the degree of advancement of the disease; the age, body weight, general health, gender and diet of the individual; the time and route of administration; and other medications the individual is taking. Optimal dosages may be established using routine testing and procedures that are well known in the art.

The amount of each combination partner that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone. Frequency of dosage may vary depending on the compound used and the particular condition to be treated or prevented. Patients may generally be monitored for therapeutic effectiveness using assays suitable for the condition being treated or prevented, which will be familiar to those of ordinary skill in the art.

The present invention further provides a commercial package comprising, as therapeutic agents, the combination of the invention, together with instructions for simultaneous, separate or sequential administration thereof for use in the delay of progression or treatment of a cancer.

Methods for Treating

Provided herein is a method for treating or preventing cancer in a subject in need thereof comprising administering to the subject a therapeutically effective amount of a pharmaceutical combination of the invention, i.e., a pharmaceutical combination comprising: (a) Compound (I), or a pharmaceutically acceptable salt thereof, (b) Compound (II), or a pharmaceutically acceptable salt thereof, and (c) an antimetabolite antineoplastic agent.

In an embodiment, provided herein is a method for treating cancer in a subject in need thereof comprising administering to the subject a therapeutically effective amount of a combination of the invention.

In an embodiment, the antimetabolite antineoplastic agent is selected from the group consisting of 5-fluorouracil, 5-fluorodeoxyuridine, 5-fluorodeoxyuridine monophosphate, cytarabine, 5-azacytidine, gemcitabine, mercaptopurine, azathioprine, thioguanine, pentostatin, erythrohydroxynonyladenine, fludarabine phosphate, cladribine, methotrexate, and pharmaceutically acceptable salts thereof.

In a further embodiment, the antimetabolite antineoplastic agent is 5-fluorouracil.

In an embodiment of any of the methods provided herein, the cancer is a solid tumor. The term "solid tumor" especially means melanoma, breast cancer, ovarian cancer, colorectal cancer, and generally gastrointestinal tract, cervix cancer, lung cancer (including small-cell lung cancer and non-small cell lung cancer), head and neck cancer, bladder cancer, or prostate cancer. The present combination inhibits the growth of solid tumors and also liquid tumors. Further, depending on the tumor type and particular combination used, a decrease of the tumor volume can be obtained. The combination of the invention disclosed herein is also suited to prevent the metastatic spread of tumors and the growth or development of micrometastases. The combination of the invention disclosed herein is suitable for the treatment of poor prognosis patients, especially such poor prognosis patients having colon cancer, rectal cancer, colorectal cancer, breast cancer, stomach cancer or pancreatic cancer.

In another embodiment of any of the methods provided herein, the cancer is selected from a benign or malignant tumor of the lung (including small cell lung cancer and non-small-cell lung cancer), bronchus, prostate, breast (including sporadic breast cancers and sufferers of Cowden disease), pancreas, gall bladder, gastrointestinal tract, colon, rectum, colon carcinoma, colorectal cancer, thyroid, liver, biliary tract, intrahepatic bile duct, hepatocellular, adrenal gland, stomach, gastric, central or peripheral nervous system (including astrocytoma, neuroblastoma, glioma, glioblastoma, and schwannoma), neuroendocrine, endometrial, kidney, renal pelvis, bladder, uterus, cervix, vagina, ovary, multiple myeloma, esophagus, nose, neck or head, brain, oral cavity and pharynx, larynx, small intestine, a melanoma, villous colon adenoma, a sarcoma (including osteosarcoma, fibrosarcoma or rhabdomyosarcoma, and Kaposi's sarcoma), a neoplasia, a neoplasia of epithelial character, a mammary carcinoma, basal cell carcinoma, squamous cell carcinoma, actinic keratosis, polycythemia vera, essential thrombocythemia, thyroid follicular cancer, a leukemia (including acute myelogenous leukemia, chronic myelogenous leukemia, lymphocytic leukemia, myeloid leukemia, meningeal leukemia, and promyelocytic leukemia), a lymphoma (including non-Hodgkin lymphoma, Hodgkin's lymphoma, mantle cell lymphoma, chronic lymphocytic leukaemia, B-cell lymphoma, T-cell lymphoma, hairy cell lymphoma, and Burkett's lymphoma), myelodysplastic syndrome, choriocarcinoma, rhabdoid cancer, seminoma, teratocarcinoma, xeroderma pigmentosum; retinoblastoma, keratoctanthoma, myelofibrosis with myeloid metaplasia, Waldenstroem disease, and Barret's adenocarcinoma.

In another embodiment, the cancer is colon cancer, rectal cancer, colorectal cancer, breast cancer, stomach cancer, or pancreatic cancer.

In another embodiment, the cancer is characterized by one or more of CDK4 mutation, CDK6 mutation, CDK4 overexpression, CDK6 overexpression, PIK3CA mutation, and PIK3CA overexpression. In a further embodiment, the cancer is characterized by activating mutations in one or more of BRAF mutation, KRAS mutation, CDK6, CDK4, and PIK3CA.

The method of treating cancer according to the invention may comprise (i) administration of the agent (a) in free or pharmaceutically acceptable salt form, (ii) administration of agent (b) in free or pharmaceutically acceptable salt form, and (iii) administration of agent (c) in free or pharmaceutically acceptable salt form, simultaneously or sequentially in any order, in jointly therapeutically effective amounts, preferably in synergistically effective amounts, e.g., in daily or intermittent dosages corresponding to the amounts described herein. The individual combination partners of the combination of the invention may be administered separately at different times during the course of therapy or concurrently in divided or single combination forms. The invention is therefore to be understood as embracing all such regimens of simultaneous or alternating treatment and the term "administering" is to be interpreted accordingly.

The following Examples illustrate the invention described above; they are not, however, intended to limit the scope of the invention in any way. The beneficial effects of the pharmaceutical combination of the present invention can also be determined by other test models known as such to the person skilled in the pertinent art.

EXAMPLES

Example 1

I. Synthesis of (S)-Pyrrolidine-1,2-dicarboxylic acid 2-amide 1-{[5-(2-tert-butyl-pyridin-4-yl)-4-methyl-thiazol-2-yl]-amide}

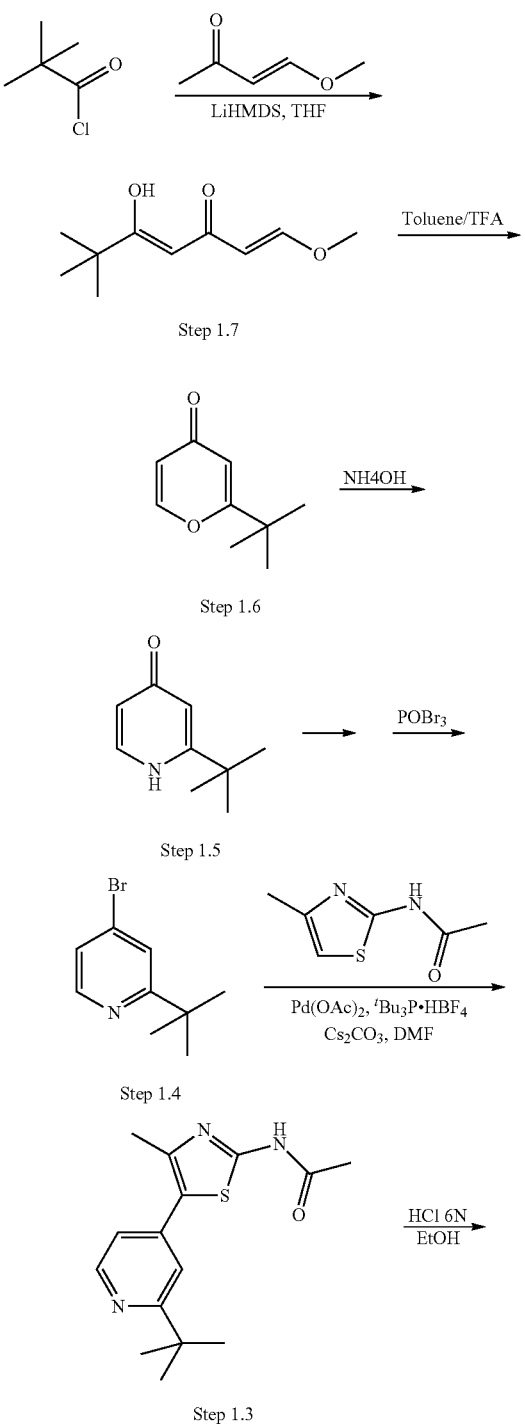

-continued

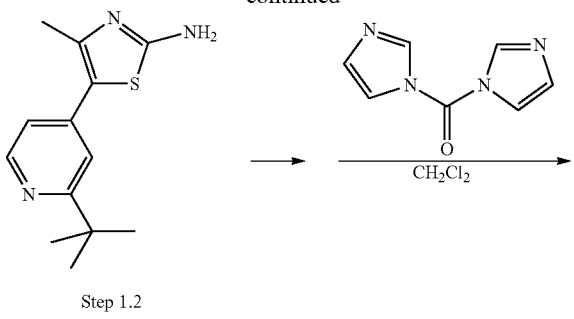

Step 1.2

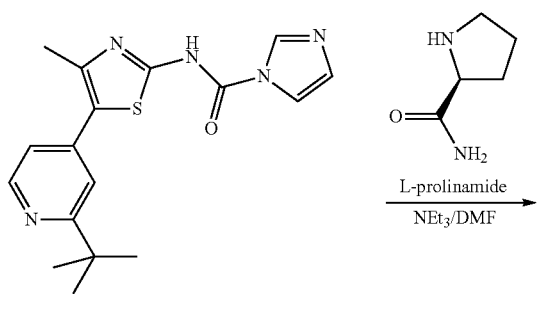

Step 1.1

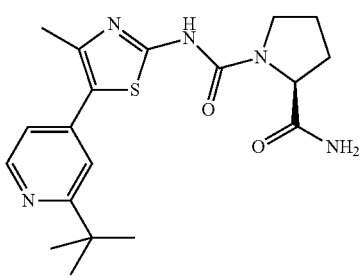

Example 1

Et₃N (1.54 mL, 11.1 mmol, 3 eq) is added to a solution of imidazole-1-carboxylic acid [5-(2-tert-butyl-pyridin-4-yl)-4-methyl-thiazol-2-yl]-amide (Step 1.1) (1.26 g, 3.7 mmol) and L-prolinamide (0.548 g, 4.8 mmol, 1.3 eq) in DMF (25 mL), under an argon atmosphere. The reaction mixture is stirred for 14 h at rt, quenched by addition of a saturated solution of NaHCO₃, and extracted with EtOAc. The organic phase is washed with a saturated solution of NaHCO₃, dried (Na₂SO₄), filtered and concentrated. The residue is purified by silica gel column chromatography (DCM/MeOH, 1:0→94:6), followed by trituration in Et₂O to afford 1.22 g of the title compound as an off-white solid: ESI-MS: 388.1 [M+H]⁺; $t_R$=2.35 min (System 1); TLC: $R_f$=0.36 (DCM/MeOH, 9:1). ¹H NMR (400 MHz, DMSO-d6) δ(ppm): 1.32 (s, 9H) 1.75-1.95 (m, 3H) 1.97-2.13 (m, 1H) 2.39 (s, 3H) 3.38-3.50 (m, 1H) 3.52-3.65 (m, 1H) 4.10-4.40 (m, 1H) 6.94 (br. s., 1H) 7.22 (d, 1H) 7.30-7.48 (m, 2H) 8.49 (d, 1H) 10.87 (br. s., 1H).

Step 1.1: Imidazole-1-carboxylic acid [5-(2-tert-butyl-pyridin-4-yl)-4-methyl-thiazol-2-yl]-amide

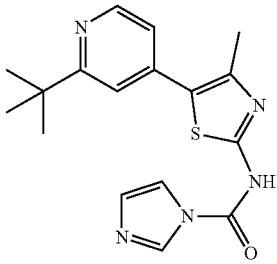 [SMILES: Cc1nc(NC(=O)n2ccnc2)sc1-c1ccnc(C(C)(C)C)c1]

A mixture of 5-(2-tert-butyl-pyridin-4-yl)-4-methyl-thiazol-2-ylamine (Step 1.2) (1 g, 4.05 mmol) and 1,1'-carbonyldiimidazole (0.984 g, 6.07 mmol, 1.5 eq) in DCM (50 mL) is stirred for 4 h at reflux and allowed to cool. The resulting precipitate is collected by filtration to provide 1.26 g of the title compound as white solid: ESI-MS: 340.2 [M−H]⁻; $t_R$=2.85 min (System 1).

Step 1.2: 5-(2-tert-Butyl-pyridin-4-yl)-4-methyl-thiazol-2-ylamine

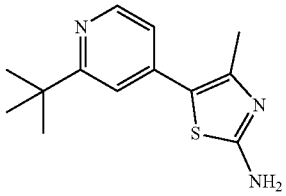 [SMILES: Cc1nc(N)sc1-c1ccnc(C(C)(C)C)c1]

A mixture of N-[5-(2-tert-butyl-pyridin-4-yl)-4-methyl-thiazol-2-yl]-acetamide (Step 1.3) (2 g, 7 mmol), a 6N aqueous solution of HCl (10 mL) and EtOH (50 mL) is stirred for 2 h at 85° C., allowed to cool, quenched by addition of a saturated solution of NaHCO₃ and extracted with DCM/MeOH (9:1, v/v). The organic phase is washed with a saturated solution of NaHCO₃, dried (Na₂SO₄), filtered and concentrated. The residue is purified by silica gel column chromatography (DCM/MeOH, 1:0→96:4) to afford 1.21 g of the title compound as a yellow solid: ESI-MS: 248.1 [M+H]⁻; TLC: $R_f$=0.36 (DCM/MeOH, 9:1).

Step 1.3: N-[5-(2-tert-Butyl-pyridin-4-yl)-4-methyl-thiazol-2-yl]-acetamide

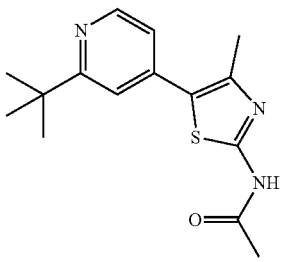 [SMILES: CC(=O)Nc1nc(C)c(-c2ccnc(C(C)(C)C)c2)s1]

A mixture of 2-acetamido-4-methylthiazole (1.2 g, 7.7 mmol, 1.1 eq), cesium carbonate (4.55 g, 14 mmol, 2 eq), tri-tert-butylphosphinium tetrafluoroborate (0.406 g, 1.4 mmol, 0.2 eq), palladium (II) acetate (0.15 g, 0.7 mmol, 0.1 eq) and 4-bromo-2-tert-butyl-pyridine (Step 1.4) (1.5 g, 7 mmol) in DMF (50 mL) is stirred for 1.5 h at 90° C. under an argon atmosphere, allowed to cool, quenched by addition of a saturated solution of NaHCO₃ and filtered through a pad of celite. The filtrate is extracted with EtOAc. The organic phase is washed with a saturated solution of NaHCO₃, dried (Na₂SO₄), filtered and concentrated. The residue is purified by silica gel column chromatography (DCM/MeOH, 1:0→97:3) to afford 2.02 g of the title compound as a yellow solid: ESI-MS: 290.1 [M+H]⁻; TLC: R_f=0.35 (DCM/MeOH, 9:1).

Step 1.4: 4-Bromo-2-tert-butyl-pyridine

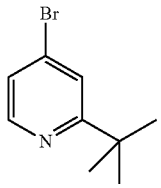

A mixture of 2-tert-butyl-1H-pyridin-4-one (Step 1.5) (4.25 g, 28 mmol) and POBr₃ (8.88 g, 31 mmol, 1.1 eq) is heated to 120° C., stirred for 15 min, allowed to cool, quenched by addition of a saturated solution of NaHCO₃ and extracted with DCM/MeOH (9:1, v/v). The organic phase is washed with a saturated solution of NaHCO₃, dried (Na₂SO₄), filtered and concentrated. The residue is purified by silica gel column chromatography (Hex/EtOAc, 95:5) to afford 5.18 g of the title compound as a yellow oil: ESI-MS: 214.0/216.0 [M+H]⁺; t_R=2.49 min (System 1); TLC: R_f=0.35 (Hex/EtOAc, 1:1).

Step 1.5: 2-tert-Butyl-1H-pyridin-4-one

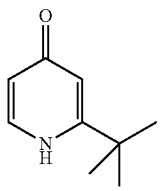

A mixture of 2-tert-butyl-pyran-4-one (Step 1.6) (5.74 g, 37.7 mmol) and a 30% aqueous solution of ammonium hydroxide (100 mL) is stirred for 1 h at reflux, allowed to cool and concentrated. The residue is triturated with MeOH (200 mL) and filtered. The filtrate is concentrated and the residue purified by silica gel column chromatography (DCM/MeOH/NH₃_aq, 94:5:1→92:7:1) to afford 4.46 g of the title compound as a yellow solid: ESI-MS: 152.0 [M+H]⁻; t_R=1.45 min (System 1); TLC: R_f=0.11 (DCM/MeOH, 9:1).

Step 1.6: 2-tert-Butyl-pyran-4-one

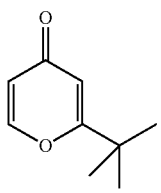

A mixture of 5-hydroxy-1-methoxy-6,6-dimethyl-hepta-1,4-dien-3-one (Step 1.7) (6.8 g, 36.9 mmol) and TFA (5.65 mL, 74 mmol, 2 eq) in benzene (250 mL) is stirred for 14 h at rt and concentrated. Purification of the residue by silica gel column chromatography (Hex/EtOAc, 1:0→75:25) provides 5.74 g of the title compound as a yellow oil: ESI-MS: 153.1 [M+H]⁺; t_R=3.21 min (System 1); TLC: R_f=0.22 (Hex/EtOAc, 1:1).

Step 1.7: 5-Hydroxy-1-methoxy-6,6-dimethyl-hepta-1,4-dien-3-one

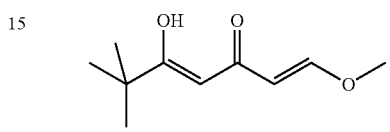

LiHMDS (1M in THF, 100 mL, 2 eq) is added dropwise to a cold (−78° C.) solution of 4-methoxy-3-buten-2-one (10 mL, 100 mmol, 2 eq) in THF (400 mL). After a 30 min stirring at −78° C., a solution of pivaloyl chloride (6.12 mL, 50 mmol) in THF (100 mL) is added. The resulting mixture is allowed to warm to rt over 2 h and quenched by addition of a saturated solution of NH₄Cl. THF is removed under vacuum. The concentrated mixture is extracted with Et₂O. The organic phase is washed with brine, dried (Na₂SO₄), filtered and concentrated. The residue is purified by silica gel column chromatography (Hex/EtOAc, 1:0→85:15) to afford 6.83 g of the title compound as a yellow oil: ESI-MS: 185.1 [M+H]⁺; TLC: R_f=0.87 (Hex/EtOAc, 1:1).

II. Synthesis of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (Compound (I) or COMPOUND A or BYL719)

The title compound is prepared in analogy to the procedure described in above, but with the following modifications. In Step 1.1, the reaction mixture is stirred for 14 h at reflux. In Step 1.2, the reaction mixture is stirred for 1 h at 85° C. and extracted with EtOAc after being quenched. In Step 1.3, the reaction mixture is stirred for 2.5 h at 120° C. In Step 1.4, the reaction mixture is stirred for 1 h at 83° C. and extracted with EtOAc after being quenched. In Step 1.5, the reaction mixture is stirred for 1 h at 65° C. and trituration in MeOH is not performed. In Step 1.6, the crude product is not purified. In Step 1.7, 3,3,3-trifluoro-2,2-dimethyl-propionyl chloride is used.

Title compound: ESI-MS: 442.0 [M+H]⁺; t_R=3.02 min (System 1); TLC: R_f=0.35 (DCM/MeOH, 9:1). ¹H NMR (400 MHz, DMSO-d6) δ(ppm): 1.60 (s, 6H) 1.70-1.95 (m, 3H) 1.99-2.16 (m, 1H) 2.40 (s, 3H) 3.38-3.51 (m, 1H) 3.51-3.69 (m, 1H) 4.10-4.40 (m, 1H) 6.95 (br. s., 1H) 7.39 (d, 2H) 7.53 (s, 1H) 8.58 (d, 1H) 10.93 (br. s., 1H)

In an alternative procedure the title compound is prepared in analogy to the procedure described above, but with the following modifications: N,N-Dimethylacetamide is used instead of DMF and the mixture is stirred at 65° C. for 2 h. In Step 1.1, phenyl chloroformate (added slowly) is used instead of 1,1'-carbonyldiimidazole and the reaction is carried out in THF in the presence of N,N-diethyl-isopropylamine at room temperature (1.5 h). In Step 1.2, the reaction mixture is heated under stirring for 5 h under (reflux) and extracted with EtOAc after being quenched. In Step 1.3, the reaction mixture is stirred for 2 h at 100° C. In Step 1.4, the reaction is run in toluene using 1.1 equivalents of POBr$_3$ and 1.1 equivalents of tripropylamine and the mixture is stirred for 2 h at 80° C. and extracted with EtOAc after being quenched. In Step 1.5, the reaction mixture is stirred for 1 h at 65° C. and trituration in MeOH is not performed. In Step 1.6, toluene is used instead of benzene and the crude product is not purified. In Step 1.7, 3,3,3-trifluoro-2,2-dimethyl-propionyl chloride is used.

Example 2

The In Vitro Effect on Proliferation of Combining the PIK3CA Inhibitor BYL719 (COMPOUND A) and the CDK4/6 Inhibitor LEE011 (COMPOUND B) with the Standard of Care Antimetabolite Antineoplastic Agent, 5-Fluorouracil (COMPOUND C) in Colorectal Cancer Cell Lines COMPOUNDS A, B, and C were dissolved in 100% DMSO (Sigma, Catalog number D2650) at concentrations of 20 mM and stored at −20° C. until use. Compounds were arrayed in drug master plates (Greiner, Catalog number 788876) and serially diluted 3-fold (7 steps) at 2000× concentration.

Colorectal cancer cell lines used for this study were obtained, cultured and processed from commercial vendors ATCC, CellBank Australia, DMSZ, ECACC, and HSRRB (Table 1). All cell line media were supplemented with 10% FBS (HyClone, Catalog number SH30071.03). Media for LIM2551 was additionally supplemented with 0.6 µg/mL Insulin (SIGMA, Catalog number 19278), 1 µg/mL Hydrocortisone (SIGMA, Catalog number H0135), and 10 µM 1-Thioglycerol (SIGMA, Catalog number M6145).

To test the effect of the combination of COMPOUND A, COMPOUND B, and COMPOUND C on cell proliferation cells were plated in black 384-well microplates with clear bottom (Matrix/Thermo Scientific, Catalog number 4332) in 50 µL media per well at cell densities between 500 and 1250 cells/well (Table 1) and allowed to incubate at 37 degrees, 5% CO2 for 24 h. After 24 h one 384-well plate per cell line was prepared for cell counting by microscopy (see below) without receiving treatment (='baseline'). The other cell plates were treated by transferring 25 nL of the 2000× compound from drug master plates using an ATS acoustic liquid dispenser (ECD Biosystems) and resulting in a final 1× concentration. COMPOUND A was used over a final concentration range of 13 nM-10 µM, COMPOUND B was used over a final concentration range of 13 nM-10 µM, and COMPOUND C was used over a final concentration range of 27 nM-20 µM (7 1:3 dilution steps). In order to assess the effect of the triple combination all individual COMPOUNDS (A, B, C), all three pair wise combinations (A+B, A+C, B+C), and the triple combination (A+B+C) were tested in the same experiment. Pair wise combinations and the triple combination were tested at a fixed ratio of 1:1 (for drug pairs) and 1:1:1 (for the drug triple) at each dilution resulting in 7 combination conditions per treatment. Additionally, negative controls (DMSO='vehicle') and positive controls (Staurosporine=killing cells, 7-point 1:2 dilution series for a dose range of 16 nM-1 µM) were transferred as treatment controls, and compounds with no efficacy in the cell lines tested were used in combinations with COMPOUND A and COMPOUND B as combination controls (combinations that do not exceed the efficacy of the more efficacious single agent='non-interacting' combinations). After compound addition 50 nL of 2 mM CellEvent Cas-

TABLE 1

Cell line information

| Cell line | Driver mutations | Source | Source Cat Num | Medium | Medium Vendor | Medium Cat Num | #Cells | Treatment [h] |
|---|---|---|---|---|---|---|---|---|
| DLD-1 | KRAS, PIK3CA | ATCC | CCL-221 | RPMI | ThermoFisher | 22400-071 | 500 | 72 |
| HCT-116 | KRAS, PIK3CA | ATCC | CCL-247 | McCoy's 5A | ATCC | 30-2007 | 500 | 72 |
| LA-180 | KRAS, PIK3CA | ATCC | CCL-187 | EMEM | ATCC | 30-2003 | 800 | 72 |
| GP2d | KRAS, PIK3CA | ECACC | 95090714 | DMEM | ATCC | 30-2002 | 900 | 72 |
| SW480 | KRAS | ATCC | CCL-228 | RPMI | ATCC | 30-2001 | 700 | 72 |
| SW837 | KRAS | ATCC | CCL-235 | RPMI | ATCC | 30-2001 | 1250 | 72 |
| LoVo | KRAS | ATCC | CCL-229 | F-12K | ATCC | 30-2004 | 1250 | 96 |
| RKO | BRAF, PIK3CA | ATCC | CCL-2577 | EMEM | ATCC | 30-2003 | 500 | 72 |
| LIM2551 | BRAF, PIK3CA | Cellbank Australia | CBA-0170 | RPMI | ATCC | 30-2001 | 1000 | 72 |
| HT-29 | BRAF, PIK3CA | ATCC | HTB-38 | McCoy's 5A | ATCC | 30-2007 | 800 | 72 |
| OUMS-23 | BRAF | HSRRB | JCRB1022 | DMEM | ATCC | 30-2002 | 900 | 72 |
| LS411N | BRAF | ATCC | CRL-2159 | RPMI | ATCC | 30-2001 | 900 | 72 |
| COLO-205 | BRAF | ATCC | CCL-222 | RPMI | ATCC | 30-2001 | 800 | 72 |
| NCI-H508 | PIK3CA | ATCC | CCL-253 | RPMI | ATCC | 30-2001 | 1000 | 72 |
| COLO-320 | | DSMZ | ACC-144 | RPMI | ATCC | 30-2001 | 800 | 72 |

Cell lines were cultured in 37° C. and 5% CO$_2$ incubator and expanded in T-75 flasks. In all cases cells were thawed from frozen stocks, expanded through ≥1 passage using 1:3 dilutions, counted and assessed for viability using a ViCell counter (Beckman-Coulter) prior to plating. To split and expand cell lines, cells were dislodged from flasks using 0.25% Trypsin-EDTA (GIBCO, Catalog number 25200). All cell lines were determined to be free of mycoplasma contamination as determined by a PCR detection methodology performed at Idexx Radil (Columbia, Mo., USA) and correctly identified by detection of a panel of SNPs.

pase-3/7 Green Detection Reagent (ThermoFisher, Catalog number C10423) were added to one of the three replicates using the HP D300 Digital Dispenser (Tecan). Caspase 3/7 induction was measured as a proxy for apoptosis induced by the treatments. Cells were treated for 72 h to 96 h depending on their doubling time (Table 1), and Caspase 3/7 activation was measured every 24 h by microscopy using an InCell Analyzer 2000 (GE Healthcare) equipped with a 4× objective and FITC excitation/emission filters. At the end of the treatment cells were prepared for cell counting by microscopy. Cells were fixed and permeabilised for 45 minutes in 4% PFA (Electron Microscopy Sciences, Catalog number 15714), 0.12% TX-100 (Electron Microscopy Sciences, Catalog number 22140) in PBS (Boston Bioproducts, Catalog number BM-220). After washing cells three times with PBS their DNA was stained for 30 minutes with Hoechst 33342 (ThermoFisher, Catalog number H3570) at a final concentration of 4 µg/mL. Cells were washed three times with PBS and then plates were heat-sealed using a PlateLoc (Agilent Technologies) with aluminum seals (Agilent Technologies, Catalog number 06644-001) and stored at 4° C. until imaging. All cells per well/treatment were captured in a single image by fluorescence microscopy using an InCell Analyzer 2000 (GE Healthcare) equipped with a 4× objective and DAPI excitation/emission filters.

Images were analyzed after adapting previously described methods (Horn, Sandmann et al. 2011, Nat. Methods 8(4): 341-346) and using the Bioconductor package EBImage in R (Pau, Fuchs et al. 2010, Bioinformatics 26(7):979-981). Objects in both channels, DAPI (for Hoechst/DNA) and FITC (for Caspase 3/7), were segmented separately by adaptive thresholding and counted. A threshold for Caspase 3/7 positive objects was defined manually per cell line after comparing negative controls (DMSO) and positive controls (Staurosporine). By analyzing 17 additional object/nuclei features in the DNA channel (shape and intensity features) debris/fragmented nuclei were identified. To this end per cell line the distributions of the additional features between positive controls (Staurosporine) and negative controls (DMSO) were compared manually. Features that could differentiate between the conditions (e.g. a shift in the distribution of a feature measurement comparing DMSO with Staurosporine) where used to define the 'debris' population versus the population of 'viable' nuclei. The debris counts were subtracted from raw nuclei counts. The resulting nuclei number was used as measure of cell proliferation ('cell count').

The compound's effect on cell proliferation was calculated from the cell counts of the treatments relative to the cell counts of the negative control (DMSO), in FIG. 1 denoted as 'Normalized cell count' (='xnorm') on the y-axis. Synergistic combinations were identified using the highest single agent model (HSA) as null hypothesis (Berenbaum 1989). Excess over the HSA model predicts a functional connection between the inhibited targets (Lehar, Zimmermann et al. 2007, Lehar, Krueger et al. 2009). The model input were inhibition values per drug dose:

$$I = 1 - \text{xnorm}$$

I: inhibition
xnorm: normalized cell count (median of three replicates)

At every dose point of the combination treatment the difference between the inhibition of the combination and the inhibition of the stronger of the two single agents was calculated (=model residuals). Similarly, to assess the synergy of triple combinations at every dose point the difference between the inhibition of the drug triple and the inhibition of the strongest drug pair was calculated. To favor combination effects at high inhibition the residuals were weighted with the observed inhibition at the same dose point. The overall combination score C of a drug combination is the sum of the weighted residuals over all concentrations:

$$C = \Sigma_{Conc}(I_{data} * (I_{data} - I_{model}))$$

$I_{data}$: measured inhibition
$I_{model}$: inhibition according to HSA null hypothesis Robust combination z-scores ($z_C$) were calculated as the ratio of the treatments' combination scores C and the median absolute deviation (mad) of non-interacting combinations:

$$z_C = C / \text{mad}(C_{zero})$$

$C_{zero}$: combination scores of non-interacting combinations $z_C$ is an indicator for the strength of the combination with:
$z_C \geq 3$: synergy
$3 > z_C \geq 2$: weak synergy
$z_C < 2$: no synergy IC50 is the compound concentration that results in 50% of the cell counts relative to DMSO. IC50 calculations (see Table 2) were done using the DRC package in R (Ritz and Streibig January 2005, Journal of Statistical Software, "Bioassay analysis using R", 12:5:1-22) and fitting a four-parameter log-logistic function to the data.

Figure 2:
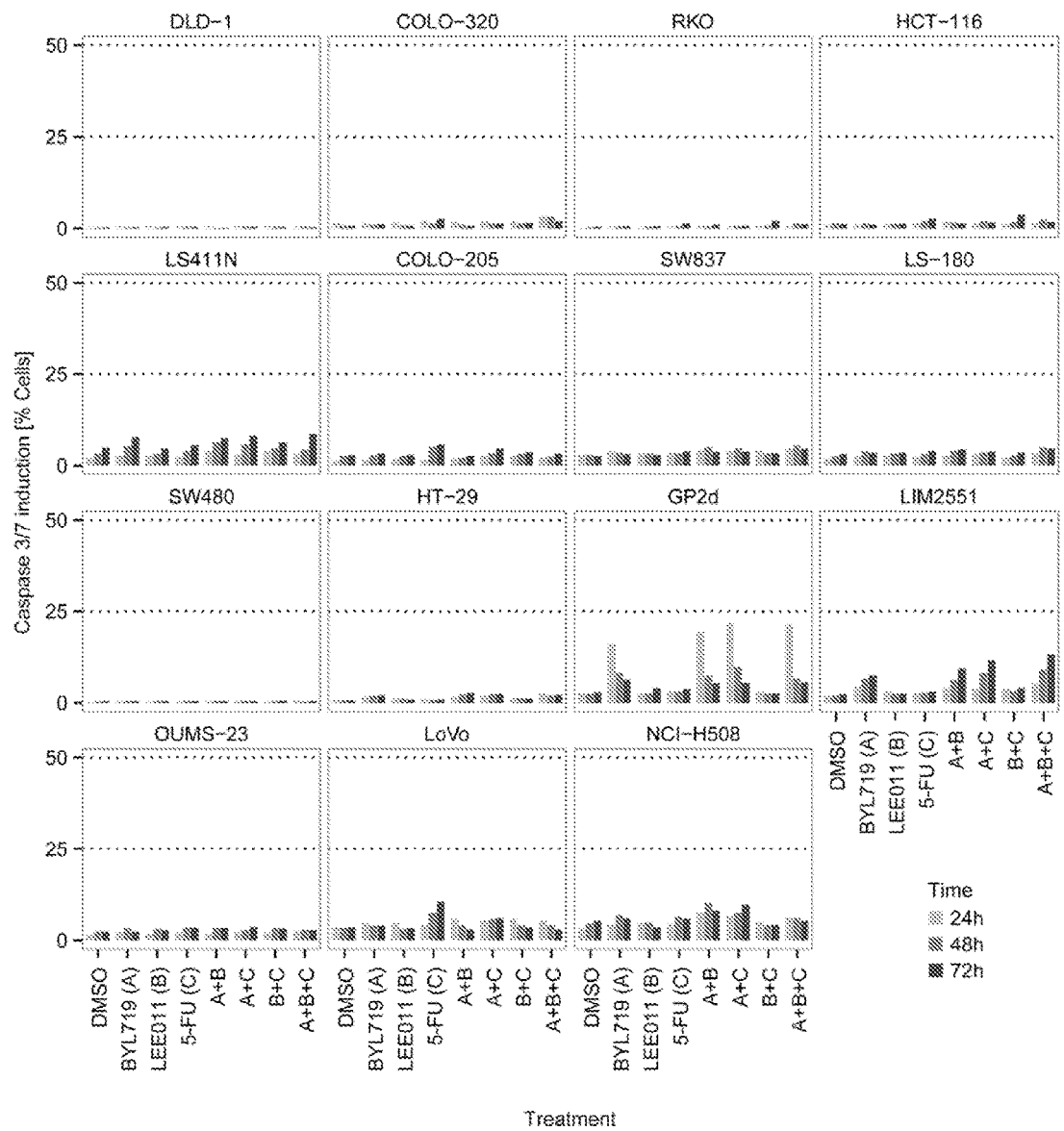
FIG. 2 shows maximum Caspase 3/7 induction for COMPOUND A, COMPOUND B, COMPOUND C, A+B, A+C, B+C, and A+B+C in 15 colorectal cancer cell lines and after 24 h, 48 h, and 72 h (different shades of grey). The x-axis indicates the treatment; the y-axis indicates the maximum Caspase 3/7 induction (% of cells) seen for each treatment.

The compound's effect on apoptosis was determined by calculating the percentage of cells with activated Caspase 3/7 per treatment and time point relative to the raw cell counts (before subtraction of debris) (y-axis in FIG. 2). Cell counts at time points that were not experimentally measured were obtained by regression analysis by fitting a linear model for log-transformed cell counts at day 0 and the end of the treatment (assuming exponential cell growth).

The efficacies of a PIK3CA inhibitor (BYL719, COMPOUND A), a CDK4/6 inhibitor (LEE011, COMPOUND B), and the standard of care 5-FU (COMPOUND C) were assessed individually and in combination in a total of 15 colorectal cancer cell lines. Cell lines were mutant in KRAS, BRAF, and/or PIK3CA, or wild type for all 3 genes (Table 1). COMPOUND A and COMPOUND B showed mostly micromolar IC50 values, with COMPOUND B being more potent across the cell lines tested. COMPOUND A only reached an IC50 in 7/15 cell lines, COMPOUND B in 13/15. COMPOUND C had micromolar IC50s in all but one cell line (SW480) (FIG. 1 and Table 2). The triple combination (A+B+C) caused synergistic inhibition (according to the HSA model) over the drug pairs in 3/15 cell lines as well as weakly synergistic inhibition in 4/15 cell lines (Table 2). The triple combination does not induce apoptosis (assessed by measuring Caspase 3/7 induction) stronger compared to the pair wise combinations (FIG. 2). Collectively, combined inhibition of PIK3CA and CDK4/6 with the standard of care 5-FU may provide an effective therapeutic modality capable of improving responses compared to each of the single agents and lead to more durable responses in the clinic.

TABLE 2

Single agent IC50 values for each compound and synergy z-score measurements for the combination of COMPOUND A, COMPOUND B, and COMPOUND C.

| Cell | IC50 COMPOUND A | IC50 COMPOUND B | IC50 COMPOUND C | Synergy z-score ($z_C$) |
|---|---|---|---|---|
| DLD-1 | >10 | 4.1 | 6.6 | 4.7 |
| COLO-320 | 8.3 | 2.8 | 2.4 | 3.8 |
| RKO | 3.9 | 1.5 | 2.1 | 3.6 |
| HCT-116 | 9.8 | 4.5 | 5.6 | 2.8 |
| LS411N | >10 | 2.1 | 4.1 | 2.7 |
| COLO-205 | >10 | 1.1 | 0.6 | 2.4 |
| SW837 | >10 | >10 | 7.7 | 2.1 |
| LS-180 | >10 | 1.8 | 14 | 1.6 |
| SW480 | >10 | 1.6 | >20 | 1.5 |
| HT-29 | 2.7 | 0.8 | 7.4 | 0.9 |
| GP2d | 0.5 | 4.5 | 3.2 | 0.7 |
| LIM2551 | 2.3 | 1.3 | 4.2 | 0.5 |
| OUMS-23 | >10 | >10 | 10.4 | 0.5 |
| LoVo | >10 | 0.8 | 5.6 | 0.1 |
| NCI-H508 | 0.5 | 0.7 | 3.3 | −1.8 |

The invention claimed is:

1. A method for treating a colorectal cancer in a subject in need thereof, comprising administering to the subject a therapeutically effective amount of a pharmaceutical combination comprising:

(a) a compound having the structure of the formula (I)

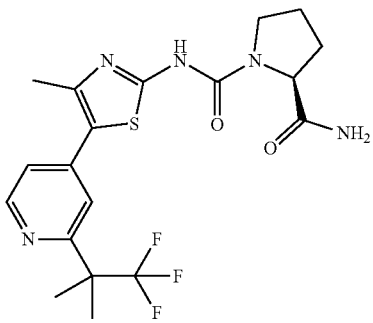

(I)

or a pharmaceutically acceptable salt thereof, (b) a compound having the structure of Formula (II)

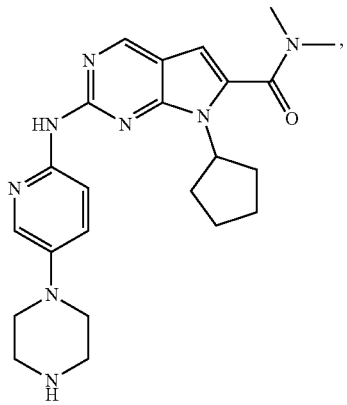

(II)

or a pharmaceutically acceptable salt thereof, and (c) an antimetabolite antineoplastic agent 5-fluorouracil or a pharmaceutically acceptable salt thereof.

2. The method according to claim 1, wherein the cancer is characterized by one or more of BRAF mutation, KRAS mutation, CDK4 mutation, CDK6 mutation, CDK4 overexpression, CDK6 overexpression, PIK3CA mutation, and PIK3CA overexpression.

* * * * *